United States Patent [19]

Wang et al.

[11] 4,360,686
[45] Nov. 23, 1982

[54] SILYLATION OF ORGANIC COMPOUNDS

[75] Inventors: Pen-Chung Wang; James M. Renga, both of Midland, Mich.

[73] Assignee: The Dow Chemical Company, Midland, Mich.

[21] Appl. No.: 298,852

[22] Filed: Sep. 3, 1981

[51] Int. Cl.$^3$ ............................ C07F 7/08; C07F 7/10; C07F 7/18
[52] U.S. Cl. .................................. 556/419; 556/442; 556/426; 556/470; 556/478; 556/436; 556/415; 556/422; 556/445; 546/14; 548/110; 260/404; 260/413; 260/398
[58] Field of Search .................. 546/14; 556/442, 426, 556/419, 470, 478, 436; 548/110; 260/404, 413, 398

[56] References Cited

PUBLICATIONS

Pierce, "Silylation of Organic Compounds", Pierce Chemical Co., Rockford, Ill., 1968, pp. 7–26, 437–445, and 481–482.
E. Nakamura et al., J. Am. Chem. Soc., 98, 2346 (1976).
T. Okada, et al. J. Organometallic Chem., 42, 117, (1972).
H. H. Hergott, et al., Synthesis, 626 (1980).

Primary Examiner—Paul F. Shaver
Attorney, Agent, or Firm—Douglas N. Deline

[57] ABSTRACT

Active hydrogen-containing compounds are silylated by contacting with trimethylsilyl trichloroacetate at elevated temperatures in the presence of an initiator.

8 Claims, No Drawings

SILYLATION OF ORGANIC COMPOUNDS

BACKGROUND OF THE INVENTION

The invention relates to a new chemical process, and more particularly to a new process for silylating organic compounds containing reactive hydrogen moieties. The products formed are trimethylsilyl compounds having various uses as heat-transfer fluids, coolants and monomers in industry. The process is further valuable as a technique for protecting reactive hydrogen-containing functional groups from attack by reagents employed in synthetic processes.

In the past, organic reactive hydrogen-containing materials have been silylated by treatment with base followed by reaction with chlorosilanes. Alternate processes involve the reaction of silylamides, silylamines, or silylethers. E. Nakamura et al., *J. Am. Chem. Soc.*, 98, 2346 (1976), disclosed the further process of reacting ethyl trimethylsilylacetate with reactive hydrogen-containing compounds in the presence of tetra-n-butyl-ammonium fluoride.

These prior art methods have the disadvantages, however, of producing stiochiometric quantities of inorganic or amine salts, requiring the use of strong acids or bases or producing unacceptably low product yields or difficult to separate product mixtures.

A suitable process for silylation or organic compounds containing active hydrogens which avoids the disadvantages of the prior art is desired.

SUMMARY OF THE INVENTION

It has now been found that active hydrogen-containing organic compounds can be readily silylated by contacting with trimethylsilyl trichloroacetate at elevated temperatures in the presence of an initiator. The process produces high yields of the desired silylated product and the non-salt by-products $CHCl_3$ and $CO_2$ are readily removed from the product and may themselves be commercially valuable.

DETAILED DESCRIPTION OF THE INVENTION

Suitable reactive hydrogen-containing compounds for use according to the invention are those having up to about 20 carbons selected from the group consisting of hydroxyl- or thiol-substituted aromatic compounds, activated hydrogen-containing carbonyl compounds such as carboxylic acids, amides or β-ketoesters and ethynyl-containing compounds.

The hydroxyl- or thiol-substituted aromatic compounds are those of the formula ArXH where Ar is an aromatic carbocyclic or aromatic nitrogen-, sulfur- or oxygen-containing heteroyclic group optionally substituted with inert substituents, and X is oxygen, sulfur or —NR— where R is lower alkyl or phenyl.

The activated hydrogen-containing carbonyl compounds are selected from the group consisting of carboxylic acids of the formula: $R_1—CO_2H$ where $R_1$ is an aromatic, aliphatic or cycloaliphatic group optionally substituted with inert substituents; amides of the formula:

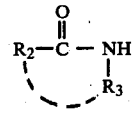

where $R_2$ and $R_3$ individually are alkyl or aryl and together may form a hydrocarbylene or hydrocarboxylene moiety, and may optionally be substituted with inert substituents; and β-ketoesters of the formula:

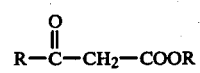

where R is as previously defined.

The ethynyl-containing compounds are those of the formula $R—C\equiv CH$ where R is as previously defined.

By inert substituent is meant a covalently attached group that does not itself react under the reaction conditions or interfer with the desired reaction of the invention.

Suitable inert substituents include lower alkyl, lower alkoxy, halo, haloalkyl, nitro and cyano.

Preferred reactive hydrogen-containing compounds are phenol itself and benzoic acid.

As previously mentioned, the reactive hydrogen-containing compound is reacted with trimethylsilyl trichloroacetate at elevated temperatures in the presence of an initiator. The reactants may be combined in any order. Generally, temperatures from about 100° C. to about 180° C. and preferably from about 110° C. to about 150° C. are employed. The reaction is conducted under atmospheric pressure although elevated or reduced pressure may also be employed. It is advantageous in order to remove gaseous by-products to employ an inert "sweep" gas of nitrogen, helium, argon, etc., to remove by-product $CHCl_3$ and $CO_2$. Reactors of glass, steel, or glass-lined steel may suitably be employed.

The reactants may be combined in any ratio, however, generally they are combined in about a stoichiometric ratio to limit contamination of the desired product by unreacted starting materials. In the presence of base, trimethylsilyl trichloroacetate begins to decompose thereby yielding trichloromethyl trimethylsilane. It is advantageous therefore to employ a slight excess of trimethylsilyl trichloroacetate to allow for some loss of reactant. Preferred are equivalent ratios of reactive hydrogen-containing compound to trimethylsilyl trichloroacetate of about 1:1 to about 1:2.

The reaction is initiated by the presence of one of several suitable initiators. Basic catalysts, such as alkali metal alkoxides, salts of a strong base and a weak acid, or non-nucleophilic organic bases are suitable. The latter class consists in practice of tertiary amines, both aliphatic and aromatic. Suitable basic catalysts include triethylamine, tributylamine, pyridine, quinoline, N,N-dimethylaminopyridine, alkali metal carbonates, acetates and alkoxides. Additional suitable initiators include stable quaternary salts such as ammonium or phosphonium quaternary salts having inert counterions. Preferably, these salts have the general formula $(R'')_4AY$ where each $R''$ is a hydrocarbon moiety, A is a quaternary nitrogen or phosphorus atom, and Y is an inert (i.e., unreactive in this process) neutralizing anion which may be inorganic, e.g., chloride, bromide, iodide, bicarbonate, sulfate, or the like, or Y may be an organic ion such as formate, acetate, benzoate, phenate, or bisphenate. The R" groups may be alkyl, aryl, alkaryl, aralkyl, or cycloalkyl. Also, two R" groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts with these and other such inorganic and organic neutralizing anions as described above. The catalytic salt may be added as such to the reaction mixture or it may be formed in situ.

The quantity of initiator compound is not critical so long as any significant amount is present and available at the reaction site. Suitably from about 0.01–1 percent of initiator based on the weight of the reactants is used. Larger amounts of initiator may be employed but may complicate the ability to produce pure product.

The initiator should be at least partially soluble in the reaction mixture and it may be advantageous in accomplishing this goal to employ an additional agent to render the initiator soluble in the reaction medium. Suitable agents, referred to hereinafter as "solubilizing agents", which are particularly suitable for use with basic catalysts include the compounds generally known as phase-transfer catalysts such as, for example, cyclic oligomers of ethylene oxide known as crown ethers. Such solubilizing agents may be employed in minor amounts, for example, in the ratio of about 0.005–1.0 mole per mole of basic catalyst.

A reaction solvent is usually not required, but use of a solvent may be employed if desired. Excess trimethylsilyl trichloroacetate can be used as the solvent. Relatively high boiling inert solvents such as N,N-dimethylformamide, sulfolane, dimethylsulfoxide, glycol diethers, and substituted aromatics such as anisole, o-dichlorobenzene, alkylated pyridines, and the like are also suitable.

In the usual operation of the process the reactants and initiator are combined in a reactor as previously described. Suitably the reactor is provided with a distillation head or other means to remove the volatile reaction by-products, chloroform and carbon dioxide.

The reaction proceeds rapidly and generally is completed in from about 1 to about 5 hours depending of course on the amounts of reactants, temperature and other reaction conditions. The products are recovered from the reaction vessel and separated from residual initiator compounds, if desired, by ordinary techniques such as distillation.

In the use of β-ketoesters, the reaction product is an enol silyl ether formed by initial abstraction of a reactive α hydrogen followed by an internal rearrangement to yield the trimethylsilyl ether according to known chemical processes.

SPECIFIC EMBODIMENTS

Having described the invention, the following examples are provided as further illustrative and are not to be construed as limiting the invention.

EXAMPLE 1

Phenol (1.17 g, 0.0125 mole), trimethylsilyl trichloroacetate (3.53 g, 0.015 mole), potassium carbonate (0.035 g) and 18-crown-6 polyether (0.066 g) were placed in a 25-ml round-bottom flask fitted with a distillation head. A dry ice receiver and dry ice trap were attached. The mixture was heated to 150° C. Gas evolution proceeded rapidly and liquid chloroform and CCl$_3$SiMe$_3$ (formed by the base-induced decomposition of trimethylsilyl trichloroacetate) collected in the dry ice trap.

After about one hour, heating was stopped and the product recovered by distillation. Analysis by nuclear magnetic resonance spectroscopy confirmed the product's identity as trimethylsiloxy benzene. Isolated yield was 88 percent.

EXAMPLES 2–17

The reaction conditions of Example 1 were substantially repeated excepting that the reactive hydrogen-containing reactant was selected from the compounds further identified in Table I. Isolated yields of the corresponding trimethylsilyl reaction products are contained in Table I.

TABLE I

| Example | Reactive Hydrogen-Containing Reactant | Product | Reaction Temperature °C. | Isolated Yield % |
|---|---|---|---|---|
| 2 | m-methylphenol | m-trimethylsiloxytoluene | 150 | 90 |
| 3 | o-chlorophenol | 2-chlorotrimethylsiloxy-chloro benzene | 150 | 85 |
| 4 | p-bromophenol | 4-bromotrimethylsiloxy benzene | 150 | 84 |
| 5 | p-nitrophenol | 4-nitrotrimethylsiloxy benzene | 150 | 80 |
| 6 | p-cyanophenol | 4-cyanotrimethylsiloxy benzene | 150 | 88 |
| 7 | p-methoxyphenol | 4-methoxytrimethylsiloxy benzene | 150 | 82 |
| 8 | p-phenylphenol | 4-phenyltrimethylsiloxy benzene | 150 | 77 |
| 9 | p-t-butylphenol | 4-t-butyltrimethylsiloxy benzene | 150 | 90 |
| 10 | 2-hydroxypyridine | 2-trimethylsiloxy pyridine | 100 | 94 |
| 11 | benzoic acid | trimethylsilyl benzoate | 150 | 88 |
| 12 | cyclopentane carboxylic acid | trimethylsilyl cyclopentane carboxylate | 100 | 90 |
| 13 | 2-oxazolidinone | 3-trimethylsilyl-2-oxazolidinone | 100 | 90 |
| 14 | caprolactam | N—trimethylsilyl caprolactam | 110 | 75 |
| 15 | p-bromothiophenol | p-((trimethylsilyl)thio)-bromo benzene | 130 | 91 |
| 16 | ethynyl benzene | ((trimethylsilyl)ethynyl)benzene | 130 | 88 |
| 17 | ethylacetoacetate | ethyl 3-(trimethylsiloxy)-2-buteneoate | 130 | 80 |

What is claimed is:

1. A process for the silylation of active hydrogen-containing compounds of up to about 20 carbons selected from the group consisting of hydroxyl- or thiol-substituted aromatic compounds, carboxylic acids, amides, β-ketoesters and ethynyl-containing compounds comprising reacting the active hydrogen-containing compound with trimethylsilyl trichloroacetate at elevated temperatures in the presence of an initiator.

2. The process of claim 1 wherein the active hydrogen-containing compound is selected from the group consisting of:
   (a) hydroxyl- or thiol-substituted aromatic compounds of the formula ArXH where Ar is an aromatic carbocyclic or an aromatic nitrogen-, sulfur- or oxygen-containing heterocyclic group, optionally substituted with inert substituents, and X is oxygen, sulfur or —NR— wherein R is lower alkyl or phenyl;
   (b) carbonyl-containing compounds of the formula $R_1$—$CO_2H$, $R_2CONR_3H$, or $RC(O)CH_2COOR$ where R is as previously defined, $R_1$ is an aromatic, aliphatic or cycloaliphatic group optionally substituted with inert substituents, $R_2$ and $R_3$ individually are alkyl or aryl and together may form a hydrocarbylene or hydrocarboxylene moiety and $R_2$ and $R_3$ may optionally be substituted with inert substituents; and
   (c) ethynyl-containing compounds of the formula RC≡CH where R is as previously defined.

3. The process of claim 2 wherein the inert substituents are selected from the group consisting of lower alkyl, lower alkoxy, halo, haloalkyl, nitro and cyano.

4. The process of claim 1 wherein the initiator comprises either a basic catalyst selected from the group consisting of alkali metal alkoxides, salts of strong bases and weak acids and non-nucleophilic organic bases or a quaternary ammonium or phosphonium salt.

5. The process of claim 4 wherein the initiator comprises a basic catalyst and a solubilizing agent.

6. The process of claim 5 wherein the basic catalyst is an alkali metal carbonate and the solubilizing agent is a cyclic polyether.

7. The process of claim 1 wherein the temperature is from about 100° C. to about 180° C.

8. The process of claim 7 wherein the temperature is from about 110° C. to about 150° C.

* * * * *